US007122615B1

(12) United States Patent
Uhrich

(10) Patent No.: US 7,122,615 B1
(45) Date of Patent: Oct. 17, 2006

(54) POLYANHYDRIDES WITH THERAPEUTICALLY USEFUL DEGRADATION PRODUCTS

(75) Inventor: Kathryn E. Uhrich, Plainfield, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/508,217

(22) PCT Filed: Sep. 10, 1998

(86) PCT No.: PCT/US98/18816

§ 371 (c)(1),
(2), (4) Date: Jun. 18, 2004

(87) PCT Pub. No.: WO99/12990

PCT Pub. Date: Mar. 18, 1999

(51) Int. Cl.
C08G 63/06 (2006.01)
(52) U.S. Cl. ............... 528/206; 424/78.17; 424/486
(58) Field of Classification Search ............ 424/78.17, 424/486; 528/206
See application file for complete search history.

(56) References Cited

U.S. PATENT DOCUMENTS

| 4,062,855 A | 12/1977 | Allan et al. ............. 260/295 PA |
| 4,126,445 A | 11/1978 | Allan et al. ..................... 71/94 |
| 4,164,560 A | 8/1979 | Folkman et al. ............... 424/22 |
| 4,298,595 A | 11/1981 | Parkinson et al. ............. 424/78 |
| 4,591,496 A | 5/1986 | Cohen et al. ................... 424/15 |
| 4,757,128 A | 7/1988 | Domb et al. ................. 528/271 |
| 4,792,598 A | 12/1988 | Ziegast ........................ 528/206 |
| 4,857,311 A | 8/1989 | Domb et al. ................... 424/78 |
| 4,868,274 A | 9/1989 | Gupta et al. ................. 528/206 |
| 4,886,870 A | 12/1989 | D'Amore et al. ........... 528/271 |
| 4,888,176 A | 12/1989 | Langer et al. ............... 424/426 |
| 4,891,225 A | 1/1990 | Langer et al. ............... 424/428 |
| 4,906,474 A | 3/1990 | Langer et al. ............... 424/428 |
| 4,916,204 A | 4/1990 | Domb et al. ................. 528/271 |
| 4,997,904 A | 3/1991 | Domb ......................... 528/272 |
| 4,999,417 A | 3/1991 | Domb ......................... 528/271 |
| 5,032,216 A | 7/1991 | Felten ......................... 156/628 |
| 5,082,925 A | 1/1992 | Shalaby et al. .............. 528/354 |
| 5,160,745 A | 11/1992 | DeLuca et al. .............. 424/487 |
| 5,175,235 A | 12/1992 | Domb et al. ................. 528/271 |
| 5,259,968 A | 11/1993 | Emert et al. ............. 252/51.5 A |
| 5,264,540 A | 11/1993 | Cooper et al. ............... 528/272 |
| 5,290,494 A | 3/1994 | Coombes et al. .............. 264/41 |
| 5,317,079 A | 5/1994 | Domb et al. ................. 528/271 |
| 5,364,725 A | 11/1994 | Wilson et al. ........... 430/108.4 |
| 5,498,729 A | 3/1996 | Domb ......................... 548/500 |
| 5,512,131 A | 4/1996 | Kumar et al. ............. 156/655.1 |
| 5,514,764 A | 5/1996 | Frechet et al. ................. 528/10 |
| 5,518,730 A | 5/1996 | Fuisz ........................... 424/426 |
| 5,545,409 A | 8/1996 | Laurencin et al. ........... 424/426 |
| 5,629,009 A | 5/1997 | Laurencin et al. ........... 424/426 |
| 5,721,131 A | 2/1998 | Rudolph et al. ....... 435/240.243 |
| 5,776,748 A | 7/1998 | Singhvi et al. .............. 435/180 |
| 5,798,115 A | 8/1998 | Santerre et al. .............. 424/423 |
| 5,837,278 A | 11/1998 | Geistlich et al. ............. 424/444 |
| 5,891,477 A | 4/1999 | Lanza et al. ................. 424/501 |
| 5,902,599 A | 5/1999 | Anseth et al. ............... 424/426 |
| 5,937,758 A | 8/1999 | Maracas et al. ............. 101/327 |
| 5,958,911 A | 9/1999 | Evans et al. ................. 514/166 |
| 5,969,020 A | 10/1999 | Shalaby et al. .............. 524/167 |
| 6,123,956 A | 9/2000 | Baker et al. ................. 424/426 |
| 6,153,212 A | 11/2000 | Mao et al. ................... 424/426 |
| 6,171,610 B1 | 1/2001 | Vacanti et al. .............. 424/426 |
| 6,280,772 B1 | 8/2001 | Pinkus ........................ 424/486 |
| 6,365,149 B1 | 4/2002 | Vyakarnam et al. ........ 424/93.1 |
| 6,468,519 B1 | 10/2002 | Uhrich ..................... 424/78.01 |
| 6,486,214 B1 | 11/2002 | Uhrich ..................... 514/772.5 |
| 6,602,915 B1 | 8/2003 | Uhrich ..................... 514/772.2 |
| 6,613,807 B1 | 9/2003 | Uhrich ..................... 514/772.5 |
| 6,685,928 B1 | 2/2004 | Uhrich et al. ............. 424/78.17 |
| 6,689,350 B1 | 2/2004 | Uhrich ..................... 424/78.17 |
| 2003/0035787 A1 | 2/2003 | Uhrich ..................... 424/78.37 |
| 2004/0038948 A1 | 2/2004 | Uhrich ........................ 514/165 |
| 2004/0044125 A1 | 3/2004 | Uhrich ........................ 525/54.1 |
| 2004/0096476 A1 | 5/2004 | Uhrich et al. ................ 424/426 |

FOREIGN PATENT DOCUMENTS

| AU | 750424 | 3/2003 |
| CA | 2393676 | 7/2002 |
| DE | 288311 | 3/1991 |
| DE | 0288387 | 3/1991 |
| EP | 0246341 | 11/1987 |
| EP | 0580386 | * 7/1992 |

(Continued)

OTHER PUBLICATIONS

"Polyanhydrides with Therapeutically Useful Degradation Products", U.S. Appl. No. 09/508,217, filed Mar. 8, 2000, 1-26.

(Continued)

Primary Examiner—Terressa Boykin
(74) Attorney, Agent, or Firm—Viksnins Harris & Padys PLLP

(57) ABSTRACT

An aromatic polyanhydride having a repeating unit with structure (I) wherein Ar is a substituted or unsubstituted aromatic ring and R is a difunctional organic moiety substituted on each Ar ortho to the anhydride group. Ortho-substituted bis-aromatic dicarboxylic acid anhydride monomers and ortho-substituted bis-aromatic dicarboxylic acid intermediates thereof are also disclosed, as well as implantable medical devices, such as scaffolding implants for tissue reconstruction, drug delivery systems prepared from the aromatic polyanhydrides, as well as therapeutic oral dosage forms and treatment methods.

42 Claims, No Drawings

FOREIGN PATENT DOCUMENTS

| | | | |
|---|---|---|---|
| EP | 0498283 | | 8/1992 |
| JP | 6255797 | | 12/1985 |
| JP | 61186309 | * | 8/1986 |
| NL | 9000237 | | 8/1991 |
| WO | WO-91/09831 | | 7/1991 |
| WO | WO-97/39738 | | 10/1997 |
| WO | WO-97/44016 A1 | | 11/1997 |
| WO | WO-97/49385 | | 12/1997 |
| WO | WO-98/36013 | | 8/1998 |
| WO | WO-99/29885 | | 6/1999 |
| WO | WO-99/36107 | | 7/1999 |
| WO | WO-00/66730 A1 | | 11/2000 |
| WO | WO-01/28492 | | 4/2001 |
| WO | WO-01/41753 A2 | | 6/2001 |
| WO | WO-02/09767 | | 2/2002 |
| WO | WO-02/09768 | | 2/2002 |
| WO | WO-02/09769 | | 2/2002 |

OTHER PUBLICATIONS

"Polyanhydrides with Therapeutically Useful Degradation Products to Promote Healing of Bone and Soft Tissue", PCT Application PCT/US98/18816, 27 Pages.

"Polyannydrides with Therapeutically Useful Degradation Products to Promote Healing of Bone and Soft Tissue", U.S. Appl. No. 09/455,861, filed Dec. 7, 1999, converted on Dec. 11, 2000 to U.S. Appl. No. 60/304,190, 25 Pages.

Aebischer, P , et al., "Basic fibroblast growth factor released from synthetic guidance channels facilitates peripheral nerve regeneration across long nerve gaps", *Journal of Neuroscience Research*, 23(3), (Jul. 1989),282-9.

Anastasiou, Theodore J., "Novel Polyanhydrides with Enhanced Thermal and Solubility Properties", *Macromolecules*, 33(17), (2000),6217-6221.

Anastasiou, Theodore J., "Novel, Degradable Polyanhydrides", *25th Annual Meeting Transactions of the Society for Biomaterials*, Abstract,(1999),79.

Anastasiou, Theodore J., "Synthesis of Novel, Degradable Polyanhydrides Containing Para-Aminosalicylic Acid as Drug Delivery Devices for Tuberculosis Treatment", *Polymer Preprints*, 41(2), (Aug. 2000),1366-1367.

Attawia, Mohamed A., "Biocompatibility Testing of Poly(anhydride-co-imides) Containing Pyromellitylimidoalanine", *The 21st Annual Meeting of the Society for Biomaterials*, Abstract,(Apr. 5-9, 1994),222.

Attawia Mohamed A., "Cytotoxicity testing of poly(anhydride-co-imides) for orthopedic applications", *Journal of Biomedical Materials Research*, 29(10), (1995),1233-1240.

Attawia, Mohamed A., "In vitro bone biocompatibility of poly (anhydride-co-imides) containing pyromellitylimidoalanine", *Journal of Orthopedic Research*, 14(3), (1996),445-454.

Attawia, Mohamed A., "Proliferation, Morphology, and Protein Expression by Osteoblasts Cultured on Poly(anhydride-co-amides)", *Journal of Biomedical Materials Research*, 48(3), (1999),322-327.

Attawia Mohamed A., "The Long Term Osteoblast Response to Poly(anhydride-co-imides): A New Degradable Polymer for Use in Bone", *Proceedings of the Fifth World Biomaterials Congress*, Toronto, Canada, (1996),113.

Beaton, Michael L., "Synthesis of a novel poly(anhydride-ester)", *The Rutgers Scholar—An Electronic Bulletin of Undergraduate Research*, vol. 3, http://www.scils.rutgers.edu/~weyang/ejournal/volume03/beatuhri/beatuhri.htm,(2001),1-7.

Bedell, Christi, "Processing and Hydrolytic Degradation of Aromatic, Ortho-Substituted Polyanhydrides", *Journal of Applied Polymer Science*, 80, (2001),32-38.

Brambley, D , et al., "Microlithography: an overview", *Advanced Materials for Optics and Electronics*, 4(2), (Mar.-Apr. 1994),55-74.

Branch, D W., "Microstamp patterns of biomolecules for high-resolution neuronal networks", *Medical & Biological Engineering & Computing*, 36(1), (Jan. 1998),135-41.

Brown, Joseph P., "A Polymeric Drug for Treatment of Inflammatory Bowel Disease", *Journal of Medicinal Chemistry*, 26(9), (1983),1300-1307.

Brown, L , et al., "Transdermal delivery of drugs", *Annual Review of Medicine*, 39, (1988),221-9.

Campo, Cheryl J., "Polyanhydrides: the effects of ring substitution changes on polymer properties", *Polymer Bulletin*, 42, (1999),61-68.

Chafi, N., "Dosage Form with Salicylic Acid Attached to the Polyanhydride Polymer Dispersed in an Eudragit Matrix", *International Journal of Pharmaceutics*, 52, (1989),203-211.

Chen, G , "Effect of protein and cell behavior on pattern-grafted thermoresponsive polymer", *Journal of Biomedical Materials Research*, 42(1), (Oct. 1998),8-44.

Conix, Andre , "Aromatic Polyanhydrides, a New Class of High Melting Fiber-Forming Polymers", *Journal of Polymers Science*, XXIX, (1958),343-353.

Conix, Andre , "New High-Melting Fibre-Forming Polymers", *Die Makromolekulare Chemie*, XXIV, (1957),76-78.

Conix, Andre , "Poly (1,3-bis (p carboxyphenoxy)—Propane anhydride)", *Macromolecular Synthesis*, 2, (1996),95-99.

Davaran, Soodabeh , "Release of 5-amino Salicylic Acid from Acrylic Type Polymeric Prodrugs Designed for Colon-specific Drug Delivery", *Journal of Controlled Release*, 58(3), (1999),279-287.

Davies, M. C., "The Analysis of the Surface Chemical Structure of Biomedical Aliphatic Polyanhydrides Using SPX and ToF-SIMS", *Journal of Applied Polymer Science*, 42 (1991) Mar. 20, No. 6, New York, US, (Mar. 20, 1991),1597-1605.

Delamarche, Emmanuel , et al., "Patterned delivery of immunoglobulins to surfaces using microfluidic networks", *Science*, 276(5313), (May 2, 1997),779-781.

Dewez, J. L., et al., "Adhesion of mammalian cells to polymer surfaces: from physical chemistry of surfaces to selective adhesion on defined patterns", *Biomaterials*, 19(16), (Aug. 1998),1441-1445.

Domb, A J., "Polyanhydrides. I. Preparation of High Molecular Weight Polyanhydrides", *Journal of Polymer Science: Part A: Polymer Chemistry*, vol. 25, (1987),pp. 3373-3386.

Domb, Abraham J., "Synthesis and Characterization of Biodegradable Aromatic Anhydride Copolymers", *Macromolecules*, 25, (1992),12-17.

Dontha, N , "Generation of biotin/avidin/enzyme nanostructures with maskless photolithography", *Analytical Chemistry*, 69(14), (Jul. 15, 1997),2619-25.

Dukovic, Gordana, "Novel degradable poly(anhydride-esters) for controlled drug release", *The Rutgers Scholar—An Electronic Bulletin of Undergraduate Research*, 1, http://www.scils.rutgers.edu/~weyang/ejournal/volume01/uhriduko/uhriduko.htm,(1999),1-10.

Erdmann, Laura , "Chapter 5: Polymeric Prodrugs: Novel Polymers with Bioactive Components", *In: Tailored Polymeric Materials for Controlled Delivery Systems*, I. McCulloh, et al., (Editors), ACS Symposium Series 709, American Chemical Society: Washington, D.C.,(1998),83-91.

Erdmann, Laura , "Degradable poly(anhydride ester) implants: effects of localized salicylic acid release on bone", *Biomaterials*, 21(24), (2000),2507-2512.

Erdmann, Laura , "Polymer Prodrugs with Pharmaceutically Active Degradation Products", *Polymer Preprints*, 38(2), (1997),570-571.

Erdmann, Laura , et al., "Polymer Prodrugs with Pharmaceutically Active Degreadation Products", *Dept. of Chemistry, Rutgers University*, Piscataway, NJ 08855-0939, 570-571.

Erdmann, Laura , "Polymeric Prodrugs: Novel Polymers for Delivery of Salicylic Acid", *Annals of Biomedical Engineering*, 26 (Suppl. 1), Abstract No. PB.26, Annual Fall Meeting,(1998),S-124.

Erdmann, Laura , et al., "Polymeric Prodrugs: Novel Polymers with Bioactive Components", *ACS SYMPOSIUM SERIES*, vol. 709, Conference: Tailored polymeric materials for controlled delivery systems- Symposium, Development from a symposium sponsored by the Division of Polymer Chemistry at the 214th National Meeting of the American Chemical Society, Las Vegas, Nevada, Sep. 7-11, 1997,(1998),83-91.

Erdmann, Laura, "Polymeric Salicylic Acid: In Vitro and In Vivo Degradation", *Polymer Preprints*, 39(2), (1998),224-225.

Erdmann, Laura, "Synthesis and degradation characteristics of salicylic acid-derived poly(anhydrid-esters)", *Biomaterials*, 21(19), (Oct. 2000),1941-1946.

Giammona, G., "Polymeric Prodrugs alpha beta poly-hyroxyethyl-d1-aspartamide as macromolecular carrier for some non-steroidal anti-inflammatory agents", *Abstracts from Database BIOSIS Online, Biosciences Information Service*, Philadelphia, PA, Original Publication from the International Journal of Pharmaceutics (Amsterdam),(1989),1 page.

Giammona, G., "Polymeric Prodrugs Alpha Beta Poly-N-hydroxyethyl-DL-aspartamide as a Macromolecular Carrier for Some Non-Steroidal Anti-inflammatory Agents", *International Journal of Pharmaceutics*, 57, (1989),55-62.

Gouin, S , et al., "New Polyanhyudrides Made from a Bile Acid Dimer and Sebacic Acid: Synthesis, Characterization and Degradation", *Macromolecules*, 33, (2000),5379-5383.

Herbert, C B., "Micropatterning gradients and controlling surface densities of photoactivatable biomolecules on self-assembled monolayers of oligo(ethylene glycol) alkanethiolates", *Chemistry & Biology*, 4(10), (Oct. 1997),731-7.

IBIM, S. , "Controlled Release Based on Poly(anhydride-co-imides)", *Proc. Intern. Symp, Control. Rel. Bioact. Mater.*, 22, (1995),2 pgs.

IBIM, S M., "Poly(anhydride-co-imides): In Vivo Biocompatibility in a rat model", *Biomaterials*, 19(10), (1998),941-951.

IBIM, S E., "Preliminary in vivo report on the osteocompatibility of poly(anhydride-co-imides) evaluated in a tibial model.", *Journal of Biomedical Material Research*, 43(4), (Winter 1998),374-379.

Ito, Y , "Micropatterned immobilization of epidermal growth factor to regulate cell function", *Bioconjugate Chemistry*, 9(2), (Mar.-Apr. 1998),277-82.

James, C D., "Patterned Protein Layers on Solid Substrates by Thin Stamp Microcontact Printing", *Langmuir*; 14(4), (1998),741-744.

Jiang, H. L., "Synthesis, Characterization and In Vitro Degradation of a New Family of Alternate Poly(ester-anhydrides) Based on Aliphatic and Aromatic Diacids", *Biomaterials*, 22(3), (2001),211-218.

Jucker, M , et al., "Fetal rat septals cells adhere to and extend processes on basement membrane, laminin, and a synthetic peptide from the laminin A chain sequence", *Journal of Neuroscience Research*, 28(4), (Apr. 1991),507-17.

Kleinfeld, D , "Controlled outgrowth of dissociated neurons on patterned substrates", *Journal of Neuroscience*, 8(11), (Nov. 1998),4098-120.

Krogh-Jespersen, E , "Synthesis of a Novel Aromatic Polyanhydride Containing Aminosalicylic Acid" , *Polymer Preprints*, 41 (1), (2000),1048-1049.

Langer, Robert , "New Methods of Drug Delivery", *Science*, 249(4976), (Sep. 1990),1527-1533.

Laurencin, C T., "Poly(andrides-co-imides): In Vivo Biocompatibility Study", *23rd Annual Meeting of the Society for Biomaterials*, New Orleans, LA, (1997),483.

Laurencin, C T., "The Biocompatibility of Poly(anhydride-co-imides): High Strength Polymers for Controlled Drug Delivery", *Proc. 24th Int'l Symp. Control. Rel. Bioact. Mater.*, (1997),973-974.

Laurencin, C T., "The Bone Biocompatibility of Poly(anhydride-co-imides)—A new generation degradable Polymer for Orthopedic Applications", *41st Annual Meeting of the Orthopedic Research Society*, Orlando, FL, (1995),143-24.

Longer, Mark A., "Sustained-Release Drug Delivery Systems", *Remington's Pharmaceutical Sciences, 18th Edition, Chapter 91*, (1990),1676-1693.

Macedo, B , et al., "The in vivo Responce to a Bioactive Biodegradable Polymer", *Journal of Dental Research*, 78, Abstract No. 2827,(1999),459.

Macedo, B , "the In Vivo Response to Bioactive Polyanhydride Monofilament", *Journal of Dental Research*, 79 (Abstract No. 3872), (2000),627.

Pinther, P. , "Synthesis of Polyanhydrides Containing Ester Groups", *Die Makromolekulare Chemie, Rapid Communications*, 11(8), (Aug. 1990),403-408.

Schacht, E., "Polymers for Colon Specific Drug Delivery", *Journal of Controlled Release*, 39, (1996),327-338.

Schmalenberg, K , "Microlithographic patterning of polymer substrates for directed neuronal", *Polymeric Materials Science Engineering*, 81, Fall Meeting, Aug. 22-26, 1999, New Orleans, LA,(1999),97.

Schmalenberg, K , "Patterned Polymer Substrates for directing Neuronal Growth", *ACS Regional Mid-Atlantic Research Meeting*, (1999).

Schmalenberg, K , "Patterning of polymer substrates for directed neuronal growth studies", *Laboratory for Surface Modification*, (Mar. 18, 1999).

Schmalenberg, K , "Thin Stamp Microcontact Patterned Printing of Protein Layers on Polymer Substrates", *Transactions: Twenty-Fifth Annual Meeting of the Society for Biomaterials*, Apr. 28-May 2, 1999.

Seidel, J O., "Erosion of Poly(anhydride-co-imides): A Preliminary Mechanistic Study", *J. Appl. Polym. Sci.*, 62(8), (1996),1277-1283.

Shen, E , "Morphological Characterization of Erodible Polymer Carriers for Drug Release", *Proc. 26th Int'l Symp. Control. Rel. Bioact. Mater.*, (1999),717-718.

Spargo, B. J., et al., "Spatially controlled adhesion, spreading, and differentiation of endothelial cells on self-assembled molecular monolayers", *Proceedings of the National Academy of Science USA*, 91(23), (Nov. 8, 1994),11070-11074.

St. John, P M., "Diffraction-based cell detection using a microcontact printed antibody grating", *Analytical Chemistry*, 70(6), (Mar. 15, 1998), 1108-11.

Tashiro, K , et al., "A synthetic peptide containing the IKVAV sequence from the A chain of laminin mediates cell attachment, migration, and neurite outgrowth", *Journal of Biological Chemistry*, 264(27), (Sep. 25, 1989),16174-82.

Uhrich, K E., "Chemical Changes during in vivo degradation of poly(anhydride-imide) matrices", *Biomaterials*, 19(22), (1998),2045-2050.

Uhrich, K E., "Degradation of poly(anhydride-co-imides): Novel Polymers for Orthopedic Applications", *Mat. Res. Soc. Symp. Proc.*, 394, (1995),41-46.

Uhrich, K E., "In Vitro Degradation Characteristics of Poly(anhydride-imides) Containing Pyromellitylimidoalanine", *J. Appl. Polymer Sci., Part A, Polym. Chem.*, 34 (7), (1996),1261-1269.

Uhrich, K E., "In Vitro Degradation Characteristics of Poly(anhydride-imides) Containing trimellitylimidoglycine", *J. Appl. Polymer. Sci.*, 63 (11), (1997),1401-1411.

Uhrich, K E., "Poly(anhydride-ester) Degradation: Mechanical Changes and Correlation to Antibiotic Release", *American Chemical Society, Abstacts of Papers, Part 2, Abstract No. 121*, 221st ACS National Meeting, San Diego, CA,(2001),Abstract 121.

Uhrich, K E., "Synthesis and Characterization of Degradable poly(anhydride-co-imides)", *Macromolecules*, 28 (7), (1995),2184-2193.

Uhrich, K E., "Synthesis and Characterization of poly(anhydride-co-imides): Solution Polycondensation of Biodegradable Polymers Derived from Amino Acids", *Proc. of the American Chemical Society, Division of Polymeric Materials: Science and Engineering*70, Spring Meeting, San Diego, CA,(1994),239-240.

Uhrich, K E., "Synthesis of Aminosalicylate-based polyanhydride Prodrugs: Esters, Amides, and Azos", *American Chemical Society, Abstracts of Papers, Part 2, Abstract No. 407*, 222nd ACS National Meeting, Chicago, IL,(2001),Abstract 407.

Woo, G L., "Biological Characterization of a Novel Biodegradable Antimicrobial Polymer Synthesized with Fluoroquinolones", *J Biomed Mater Res. 59*, (2002),pp. 35-45.

\* cited by examiner

POLYANHYDRIDES WITH THERAPEUTICALLY USEFUL DEGRADATION PRODUCTS

TECHNICAL FIELD

The present invention relates to biocompatible aromatic polyanhydrides having improved degradation properties and processability and unique therapeutic properties. In particular, the present invention relates to aromatic polyanhydrides produced from ortho-substituted bis-aromatic carboxylic acid anhydrides. The present invention also relates to ortho-substituted bis-aromatic dicarboxylic acids useful in the preparation of the aromatic polyanhydrides of the present invention.

BACKGROUND ART

Biocompatible and biodegradable aromatic polyanhydrides are disclosed by U.S. Pat. Nos. 4,757,128 and 4,997,904. However, unless incorporated into a copolymer containing a more hydrophilic monomer, such as sebacic acid, the aromatic polyanhydrides of the prior art have slow degradation times as well as relatively insoluble degradation products. A major drawback to the prior art aromatic polyanhydrides is their insolubility in most organic solvents.

Biocompatible and biodegradable aromatic polyanhydrides prepared from para-substituted bis-aromatic dicarboxylic acids are disclosed by U.S. Pat. No. 5,264,540. The para-substitution pattern results in higher melt and glass transition temperatures and decreased solubility, thus ultimately making these para-substituted polymers difficult to process.

A need exists for biocompatible and biodegradable aromatic polyanhydrides having improved degradation and processing properties, as well as therapeutic utilities.

SUMMARY OF THE INVENTION

This need is met by the present invention. It has now been discovered that the preparation of aromatic polyanhydrides from ortho-substituted bis-aromatic carboxylic acid anhydrides disrupts the crystallinity of the resulting polymer, enhancing solubility and processability, as well as degradation properties. Therefore, according to one aspect of the present invention, an aromatic polyanhydride is provided having a repeated unit within the structure of Formula I:

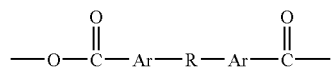
(I)

wherein Ar is a substituted or unsubstituted aromatic ring and R is a difunctional organic moiety substituted on each Ar ortho to the anhydride group. Ar and R are preferably selected so that the hydrolysis products of the polyanhydrides have a chemical structure resembling pharmaceutically-active materials, particularly salicyclates such as aspirin, non-steroidal anti-inflammatory naphthyl or phenyl propionates such as ibuprofen, ketoprofen, naproxen, and the like, or other aromatic anti-inflammatory compounds such as indomethacin, indoprofen, and the like. In particular, Ar is preferably a phenyl group and R is preferably —Z$_i$— R$_1$—Z$_{1-}$ in which R$_1$ is a difunctional moiety and both Z$_1$'s are independently either an ether, ester, amide, anhydride, carbonate, urethane or sulfide groups. R$_1$ is preferably an alkylene group containing from 1 to 20 carbon atoms, or a group with 2–20 carbon atoms having a structure selected from (—CH$_2$—CH$_2$—O—)$_m$, (—CH$_2$—CH$_2$—CH$_2$—O—)$_m$, and (—CH$_2$—CHCH$_3$—O—)$_m$.

Ortho-substituted bis-aromatic carboxylic acid anhydrides of the present invention are novel and non-obvious intermediate compounds having utility in the preparation of the aromatic polyanhydrides of the present invention. Therefore, according to another aspect of the present invention, ortho-substituted bis-aromatic carboxylic acid anhydrides are provided having the structure of Formula II:

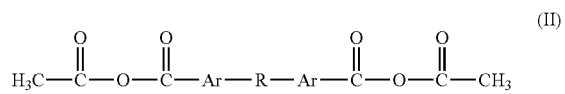
(II)

wherein Ar and R, and the preferred species thereof, are the same as described above with respect to Formula I and R is substituted on each Ar ortho to the anhydride group.

The present invention also includes ortho-substituted bis-aromatic dicarboxylic acids, which are novel and non-obvious intermediate compounds having utility in the preparation of ortho-substituted bis-aromatic carboxylic acid anhydrides. Therefore, according to another aspect of the present invention, an ortho-substituted bis-aromatic dicarboxylic acid is provided having the structure of HOOC—Ar—R—Ar—COOH, wherein Ar and R, and the preferred species thereof, are the same as described above with respect to Formula I, and R is substituted on each Ar ortho to each carboxylic acid group.

The aromatic polyanhydrides of the present invention meet the need for moldable biocompatible biodegradable polymers. Therefore, the present invention also includes implantable medical devices containing the aromatic polyanhydrides of the present invention. When Ar and R are selected so that the aromatic polyanhydride hydrolyzes to form therapeutic salicyclates, the aromatic polyanhydrides have potential uses as biocompatible, biodegradable scaffolding implants for tissue reconstruction in which the degradation products have anti-thrombogenic qualities.

In addition, the aromatic polyanhydrides that hydrolyze to form therapeutic salicyclates have potential uses as anti-inflammatory dosage forms, including dosage forms for oral administration, particularly in the treatment of digestive disorders, including bowel disorders such as inflammatory bowel disease, Crohn's disease, and the like. Ar and R may also be selected so that the aromatic polyanhydrides hydrolyze to form therapeutic non-steroidal anti-inflammatory naphthyl and phenyl propionates that resemble compounds such as ibuprofen, ketoprofen, naproxen, and the like, and other aromatic anti-inflammatory compounds such as indomethacin, indoprofen, and the like.

Therefore, the present invention also includes a method for treating inflammation by administering to a patient in need thereof a quantity of the aromatic polyanhydride of the present invention in which Ar and R are selected so that aromatic polyanhydride hydrolyzes to form therapeutic salicyclates at the site of inflammation in an amount effective to relieve the inflammation. The aromatic polyanhydrides may be administered orally. This is particularly useful in the treatment of digestive inflammation, such as inflammatory bowel disease, because the therapeutic salicyclates are formed in the gastro-intestinal tract of the patient. Methods for treating inflammation with aromatic polyanhydrides that hydrolyze to form therapeutic naphthyl or phenyl propionates are included in the present invention as well, as well as methods for treating inflammtion with aromatic polyanhydrides that hydrolyze to form indomethacin or indoprofen.

The present invention therefore also includes anti-inflammatory oral dosage forms consisting essentially of the aromatic polyanhydrides of the present invention that hydrolyze to form therapeutic salicyclates or naphthyl or phenyl propionates, or indomethacin or indoprofen, and a pharmaceutically acceptable excipient. The oral dosage forms may further include a biologically or pharmaceutically active compound to be co-administered with the therapeutic degradation products.

Ar and R may also be selected so that the aromatic polyanhydrides hydrolyzes to form therapeutic antiulcerative drugs such as rosaprostol, therapeutic antifibrotic aminobenzoates and therapeutic vasoconstricting phenylethanolamines and vasoconstricting drugs such as midodrine. Therefore, the present invention also includes a method for therapeutic treatment by administering to a patient in need thereof a quantity of the aromatic polyanhydride of the present invention in which Ar and R are selected so that aromatic polyanhydride hydrolyzes to form rosaprostol, antifibrotic aminobenzoates, vasoconstricting phenylethanolamines and midodrine. The present invention also includes oral dosage forms consisting essentially of the aromatic polyanhydrides of the present invention in which Ar and R are selected so that the aromatic polyanhydrides hydrolyze to form rosaprostol, antifibrotic aminobenzoates, vasoconstricting phenylethanolamines and midodrine.

In another embodiment of the present invention, the aromatic polyanhydrides are combined with a quantity of biologically or pharmaceutically active compound sufficient for effective site-specific or systemic drug delivery as described by Gutkowsky et al., *J. Biomater. Res.*, 29, 811–21 (1995) and Hoffman, *J. Controlled Release*, 6, 297–305 (1987). The biologically or pharmaceutically active compound may be physically admixed, embedded or dispersed in the polymer matrix. Alternatively, derivatives of biologically and pharmaceutically active compounds can be attached to repeating units of the polymers of the present invention by covalent bonds linked to an Ar ring or an R organic moiety. This provides for sustained release of the biologically or pharmaceutically active compound.

Another aspect of the present invention provides a method for site-specific or systemic drug delivery by implanting in the body of a patient in need thereof an implantable drug delivery device containing a therapeutically effective amount of a biologically or pharmaceutically active compound in combination with an aromatic polyanhydride of the present invention.

A more complete appreciation of the invention and many more other intended advantages can be readily obtained by reference to the following detailed description of the preferred embodiments and claims, which disclose the principles of the invention and the best modes which are presently contemplated for carrying them out.

DETAILED DESCRIPTION OF THE PREFERRED EMBODIMENTS

The present invention provides aromatic polyanhydrides with improved degradation properties and processability having repeating units with the structure of Formula I in which Ar and R are the same as described above with respect to Formula I. R preferably has a structure of $-Z_1-R_1-Z_1-$, in which $R_1$ is a difunctional organic moiety and both $Z_1$'s are difunctional moieties independently selected from ethers, esters, amides, anhydrides, urethanes, carbamates, carbonates, sulfides, and the like. $R_1$ may be an alkylene group containing from 1 to 20, and preferably 6, carbon atoms, or $R_1$ may be a group having from 2 to 30, and preferably 6, carbon atoms having a structure selected from $(-CH_2-CH_2-O-)_m$, $(-CH_2-CH_2-CH_2-O-)_m$, and $(-CH_2-CHCH_3-O-)_m$, or $R_1$ may have the structure $-R_2-Z_2-R_3-$, wherein $R_2$ and $R_3$ are independently alkylene groups containing from 1 to 19 carbon atoms or groups having from 2 to 18 carbon atoms having a structure selected from $(-CH_2-CH_2-O-)_m$, $(-CH_2-CH_2-CH_2-O-)_m$, and $(-CH_2-CHCH_3-O-)_m$, and $Z_2$ is selected from the difunctional moieties described above with respect to $Z_1$.

Ar may be an alkylaryl group, in which a difunctional organic moiety is positioned between each anhydride carbonyl group and the corresponding aromatic ring. Preferably, however, each carbonyl group is directly substituted on the corresponding aromatic ring.

Preferred polymers of the present invention have repeating units with the structure of Formula I in which Ar is a phenyl ring and R is selected from $-Z_1-(-CH_2-)_n-Z_1-$, $-Z(-CH_2-CH_2-O-)_m-Z_1-$, $-Z(-CH_2-CH_2-CH_2-O-)_m-Z_1-$, and $-Z(-CH_2-CHCH_3-O-)_m-Z_1-$, wherein $Z_1$ is an ether, ester or amide group and n is from 1 to 20 inclusive, and preferably is 6, and m is selected so that R has from 2 to 20, and preferably 6, carbon atoms.

The aromatic polyanhydrides of the present invention may be prepared by the method described in Conix, *Macromol. Synth.*, 2, 95–99 (1996), in which dicarboxylic acids are acetylated in an excess of acetic anhydride at reflux temperatures followed by melt condensation of the resulting carboxylic acid anhydride at 180° C. for 2–3 hours. The resulting polymers are isolated by precipitation into diethyl ether from methylene chloride. The described process is essentially the conventional method for polymerizing bis-aromatic dicarboxylic acid anhydrides into aromatic polyanhydrides.

Aromatic polyanhydrides in accordance with the present invention have weight average molecular weights of at least about 1500 daltons, up to about 35,000 daltons, calculated by Gel Permeation Chromatography (GPC) relative to narrow molecular weight polystyrene standards.

The aromatic polyanhydrides of the present invention are produced from orth-substituted bis-aromatic carboxylic acid anhydrides having the structure of Formula II in which Ar, R and the preferred species thereof are the same as described above with respect to Formula I. As noted above, ortho-substituted bis-aromatic carboxylic acid anhydrides are prepared by acetylation of the corresponding ortho-substituted bis-aromatic carboxylic acids in an excess of acetic anhydride at reflux temperatures. The dicarboxylic acids have the structure of Formula III, wherein Ar, R and the preferred species thereof are the same as described above with respect to Formula I.

The dicarboxylic acids are prepared by reacting a stiochiometric ratio of aromatic carboxylic acid having the structure $Z_2-Ar-COOH$ and a compound having a structure $Z_4-R-Z_4$ wherein Ar is a substituted or unsubstituted aromatic ring on which $Z_3$ is substituted ortho to the carboxylic acid group, R is a difunctional organic moiety and $Z_2$ and $Z_4$ are functional groups selected to provide the linkage desired between the difunctional organic moiety and the two aromatic rings.

Suitable $Z_3$ and $Z_4$ functional groups, and the manner in which they may be reacted to produce the bis-aromatic dicarboxylic acids of the present invention, may be readily determined by those of ordinary skill in the art without undue experimentation. For example, for aromatic polyanhydrides having the structure of Formula I in which Ar is a phenyl group and R is —O—(CH$_2$—)$_6$—O—, the ortho-substituted bis-aromatic dicarboxylic acid starting material may be prepared by reacting o-salicylic acid with 1,6-dibromohexane.

The aromatic polyanhydrides of the present invention can be isolated by known methods commonly employed in the field of synthetic polymers to produce a variety of useful articles with valuable physical and chemical properties. The new polymers can be readily processed by solvent casting to yield films, coatings, dishes and sponges with different geometric shapes for design of various medical implants, and may also be processed by compression molding and extrusion. Medical implant applications include the use of aromatic polyanhydrides to form shaped articles such as vascular graphs and stents, bone plates, sutures, implantable sensors, implantable drug delivery devices, stents for tissue regeneration, and other articles that decompose harmlessly within a known time period.

The polymers of the present invention include aromatic polyanhydrides having a repeating unit with the structure of Formula I in which Ar and R are selected to provide aromatic polyanhydrides that hydrolyze to form therapeutically useful salicyclates. As noted above, the salicyclates may be employed to treat inflammation, particularly digestive inflammation such as inflammatory bowel disorders. Thus, implantable or ingestible drug delivery devices of the present invention include oral dosage forms consisting essentially of the aromatic polyanhydrides of the present invention that hydrolyze to form therapeutic salicyclates, in combination with a pharmaceutically acceptable excipient. The oral dosage forms function to deliver salicyclates to the site of inflammation, either directly, or by being absorbed into the bloodstream from the digestive tract. The salicyclates may be supplemented with other therapeutic agents in the polymer matrix.

Examples of the therapeutic salicyclates include, but are not limited to, thymotic acid, 4,4-sulfinyldinailine, 4-sulfanilamidosalicylic acid, sulfanilic acid, sulfanilylbenzylamine, sulfaloxic acid, succisulfone, salicylsulfuric acid, salsallate, salicylic alcohol, orthocaine, mesalamine, gentisic acid, enfenamic acid, cresotic acid, aminosalicylic acid, aminophenylacetic acid, acetylsalicylic acid, and the like. The identification of Ar and R moieties that provide aromatic polyanhydrides that hydrolyze to form such therapeutically useful salicyclates can be readily determined by those of ordinary skill in the art without undue experimentation.

Ar and R may also be selected so that the aromatic polyanhydrides hydrolyze to form therapeutic non-steroidal anti-inflammatory phenyl and naphthyl propionates, indomethacin and indoprofen. The identification of Ar and R moieties that provide aromatic polyanhydrides that hydrolyze to form such therapeutic anti-inflammatory compounds can also be readily determined by those of ordinary skill in the art without undue experimentation.

Ar and R may also be selected so that the aromatic polyanhydrides hydrolyze to form other therapeutic compounds. For example, Ar and R may be selected to provide an aromatic polyanhydride that hydrolyzes to form the antiulcerative drug rosaprostol. Ar and R may also be selected to provide aromatic polyanhydrides that hydrolyze to form antifibrotic aminobenzoates. Ar and R may further be selected to provide polyanhydrides that hydrolyze to form the vasoconstricting drug midodrine, as well as vasoconstricting phenylethanolamines. Again, the identification of Ar and R moieties that provide aromatic polyanhydrides that hydrolyze to form such therapeutic compounds can readily be determined by those of ordinary skill in the art without undue experimentation.

Pharmaceutically acceptable excipients for oral administration are well known and include diluents such as lactose, sucrose, mannitol, sorbitol, cellulose, glycine, and the like, lubricants such as silica, talc, stearic acid and salts thereof, and the like, binders such as magnesium aluminum silicate, starches such as corn starch, methyl cellulose, and the like, and disintegrating agents such as starches, agar, and the like, as well as dyestuffs, flavors and sweeteners. The dosage forms are manufactured in a manner that is in itself well known, for example, by means of conventional mixing, granulating or dragee-making processes.

The quantity of aromatic polyanhydride that hydrolyzes to form an amount of therapeutic salicyclate effective to relieve inflammation can be readily determined by those of ordinary skill in the art without undue experimentation. The quantity essentially corresponds stiochiometrically to the amount of salicyclate known to produce an effective treatment. Oral dosage forms of aromatic polyanhydrides that hydrolyze to form other therapeutic non-steroidal anti-inflammatory compounds and other therapeutic compounds are prepared and administered in a similar manner.

The ortho-substituted aromatic polyanhydrides of the present invention exhibit desirable adhesion to cell cultures. The disruption of crystallinity is believed to improve the attachment and growth of cells and may facilitate specific interactions with proteins, peptides and cells. The aromatic polyanhydrides of the present invention are thus useful as scaffolding implants for tissue reconstruction. The polymer surfaces may also be modified by simple chemical protocols to attach specific peptides or to immobilize proteins to elicit selective cellular responses in tissue engineering applications or in implant design.

Controlled drug delivery systems may also be prepared, in which a biologically or pharmaceutically active agent is physically embedded or dispersed into the polymeric matrix, physically admixed with, or covalently bonded to the aromatic polyanhydride. Covalent bonding is accomplished by providing an aromatic polyanhydride having reactive functional groups on one or more Ar groups or R moieties and reacting the polyanhydride with a derivatized or underivatized biologically or pharmaceutically active compound capable of reacting with the functional group on the aromatic polyanhydride to form a covalent bond. Thus, biologically or pharmaceutically active compounds may be linked to aromatic polyanhydrides by means of ester groups, amide groups, and the like.

Examples of biologically or pharmaceutically active compounds suitable for the use in the present invention include acyclovir, cephradrine, malphalan, procaine, ephedrine, adriamicin, daunomycin, plumbagin, atropine, quinine, digoxin, quinidine, biologically active peptides, chlorin $e_6$, cephadrine, cephalothin, penicillin IV, nicotinic acid, chemodeoxycholic acid, chlorambucil, and the like. Biologically active compounds, for the purposes of the present invention, are additionally defined as including cell mediators, biologically active ligands, and the like. The compounds are covalently bonded to the aromatic polyanhydride by methods well understood by those of ordinary skill in the art. Drug delivery compounds may also be formed by physically blending the biologically or pharmaceutically active compound to be delivered with the aromatic polyanhydrides of the present invention using conventional techniques well-known to those of ordinary skill in the art.

The following non-limiting examples set forth hereinbelow illustrate certain aspects of the invention. All parts and percentages are by weight unless otherwise noted and all temperatures are in degrees Celsius. Except for acetic anhydride and ethyl ether (Fisher Scientific), all solvents and reagents were obtained from Aldrich Chemical. All solvents were HPLC grade. All other reagents were of analytical grade and were purified by distillation or recrystallization.

All compounds were characterized by a proton nuclear magnetic resonance (NMR) spectroscopy, infrared (IR) spectroscopy, gel permeation chromatography (GPC), high performance liquid chromatography (HPLC), differential scanning calorimetry (DSC), and thermal gravimetric analysis (TGA). Infrared spectroscopy was performed on an AT1 Mattson Genesis (M100) FTIR Spectrophotometer. Samples were prepared by solvent casting on NaCl plates. $^1H$ and $^{13}C$ NMR spectroscopy was obtained on a Varian 200 MHz or Varian 400 MHz spectrometer in solutions of $CDCl_3$ or $DMSO-d_6$ with solvent as the internal reference.

GPC was performed on a Perkin-Elmer Advanced LC Sample Processor (ISS 200) with PE Series 200 LC Pump and a PE Series LC Refractive Index Detector to determine molecular weight and polydispersity. The data analysis was carried out using Turbochrom 4 software on a DEC Celebris 466 computer. Samples were dissolved in tetrahydrofuran and eluted through a mixed bed column (PE PL gel, 5 μm mixed bed) at a flow rate of 0.5 mL/min. Samples (about 5 mg/mL) were dissolved into the tetrahydrofuran and filtered using 0.5 μm PTFE syringe filters prior to column injection. Molecular weights were determined relative to narrow molecular weight polystyrene standards (Polysciences, Inc.).

Thermal analysis was performed on a Perkin-Elmer system consisting of a TGA 7 thermal gravimetric analyzer equipped with PE AD-4 autobalance and Pyris 1 DSC analyzer. Pyris software was used to carry out data analysis on a DEC Venturis 5100 computer. For DSC, an average sample weight of 5–10 mg was heated at 10° C./min. at a 30 psi flow of $N_2$. For TGA, an average sample weight of 10 mg was heated at 20° C./min under a 8 psi flow of $N_2$. Sessile drop contact angle measurements were obtained with an NRL Goniometer (Rame-hart) using distilled water. Solutions of polymer in methylene chloride (10% wt/vol.) were spun-coated onto glass slips, at 5,000 rpm for 30 seconds.

EXAMPLES

Example I

Preparation of 1,6-Bis(o-Carboxyphenoxy)Hexane Dicarboxylic Acid

To a mixture of salicylic acid (77.12 g, 0.5580 mole) and distilled water (84 mL) sodium hydroxide (44.71 g, 1.120 mole) was added. The reaction was brought to reflux temperature before 1,6-dibromohexane (45.21 g, 0.2790 mole) was added drop-wise. Reflux was continued for 23 hours after which additional sodium hydroxide (11.17 g, 0.2790 mole) was added. The mixture was refluxed for 16 more hours, cooled, filtered, and washed with methanol. The yield was 48.8%.

Example II

Preparation of 1,6-Bis(o-Carboxyphenoxy)Hexane Monomer (o-CPH)

The dicarboxylic acid of Example I was acetylated in an excess of acidic anhydride at reflux temperature. The resulting monomer was precipitated from methylene chloride into an excess of diethyl ether. The yield was 66.8%.

Example III

Preparation of Poly(1,6-Bis(o-Carboxyphenoxy) Hexane) (Poly(o-CPH))

The monomer of Example II was polymerized in a melt condensation performed at 180° C. for 3 hours under vacuum in a reaction vessel with a side arm. The polymerization vessel was flushed with nitrogen at frequent intervals. The polymer was isolated by precipitation into diethyl ether from methylene chloride. The yield was quantitative.

All compounds were characterized by nuclear magnetic resonance spectroscopy, GPC, differential scanning calorimetry (DSC), thermal gravimetric analysis, contact angle measurements, UV spectroscopy, mass spectroscopy, elemental analysis and high pressure liquid chromatography (HPLC).

The o-CPH monomer was polymerized by melt polycondensation for 60 minutes at temperatures ranging from 100° to 300° C. Analysis of the resulting polymers by GPC indicated that the highest molecular weight, coupled with the lowest polydispersity index occurred at 260° C.

The poly(o-CPH) was generally soluble in methylene chloride and chloroform, while the poly(p-CPH) was not. The poly(o-CPH) was slightly soluble in tetrahydrofuran, acetone and ethyl acetate.

Disks of poly(o-CPH), poly(p-CPH) and, as a reference, poly(lactic acid glycolic acid) were prepared and placed in 0.1 phosphate buffer solution at 37° C. for 4 weeks. The degradation media was replaced periodically. The degradation profile was linear up to three weeks time.

In currently used polyanhydride systems, the aromatic groups are para-substituted. This substitution pattern results in higher melt and glass transition temperatures and decreased solubility, thus ultimately making these para-substituted polymers difficult to process.

Poly(o-CPH), unlike poly(p-CPH), has both a lower melting point (65° C. vs. 143° C.) and glass transition temperature (35° C. vs. 47° C.). It is also possible to solution cast poly(o-CPH) using low-boiling solvents whereas poly(p-CPH) is relatively insoluble in most organic and aqueous solvents. This structural modification gives a polymer whose hydrolysis products are chemically similar to aspirin. Aspirin is an anti-inflammatory agent derived from salicylic acid, which is one of the reagents used to synthesize the inventive polyanhydrides. Therefore, the degradation products of this polymer may actually aid in patient recovery. Because of pliability and ease of processing, the aromatic polyanhydrides of the present invention have great potential as polymer scaffolds for wound healing.

Example IV

Preparation of 1,3-bis(o-carboxyphenoxy)propane dicarboxylic acid 1,3-dibromopropane (14.7 mL, 0.145 mole) was added to a mixture of salicylic acid (40.0 g, 0.290 mole), distilled water (44 mL) and sodium hydroxide (23.2 g, 0.580 mole) using the method described in Example I. After 4 hours, additional sodium hydroxide (5.79 g, 0.145 mole) was added to the reaction mixture. Reflux was continued for another 4 hours, after which the mixture was cooled, filtered and washed using the methods described in Example I. The yield was 37.7%

Example V

Preparation of poly(1,3-bis(o-carboxyphenoxy)propane)

The dicarboxylic acid of Example IV was acetylated using the methods of Example II. The acetylated dicaboxylic acid was then polymerized using the methods described in Example III. The resulting polymer had a $M_w$ of 8,500 daltons and a polydispersity of 2.3.

Contact angle measurements on solvent-cast films demonstrated that the hexyl chain of the polymer of Example III increased the surface hydrophobicity relative to the shorter propyl chain of the polymer of Example V. A comparison of thermal characteristics emphasized the effects of lengthening the alkyl chain. In particular, the polymer of Example III has a $T_g$ of 34° C. and a $T_d$ of 410° C., while the polymer of Example V had a $T_g$ of 50° C. and a $T_d$ of 344° C. Thus, the hexyl chain decreased the glass transition temperature ($T_g$) relative to the propyl chain, reflecting the increased flexibility of the polymer chain. The opposite trend was observed for decomposition temperatures ($T_d$), with the longer alkyl chain increasing the $T_d$.

Optimum polycondensation conditions were determined for the polymer of Example III. Optimum conditions were defined as those that yielded a crude polymer with the highest molecular weight and highest $T_g$. Higher reaction temperatures decreased the $M_w$ values (measured by GPC) with a concurrent increase in polydispersity. As expected for a condensation polymerization, longer reaction times yielded polymers with higher molecular weights. However, over longer reaction times, there appeared a subsequent decrease in $T_g$. Based on these results, the optimum conditions were defined as temperatures of 220° C. for 150 minutes under a vacuum.

Example VI

Preparation of 1,8-bis[o-(benzylcarboxy)carboxy phenyl]octane dicarboxylic acid ester The initial synthesis of poly(anhydride-ester) dicarboxylic acid monomers was attempted using the same methodology used for the poly(anhydride-ether) dicarboxylic monomers of Example III. It was found, however, that the reactivity of the phenol was enhanced by benzylation of the carboxylic acid group. In addition, the solubility of benzyl salicylate in organic media increased the ability of the reaction to move forward.

Thus, benzyl salicylate (1.530 g, 6.720 mmole) and distilled tetrahydrofuran were combined under an inert atmosphere in a reaction flask. An ice-salt bath was placed under the reaction flask and the addition of 60% sodium hydride (0.4840 g, 12.10 mmole) followed. After one hour, sebacoyl chloride (0.7850 g, 3.280 mmole) was added drop-wise to the 0° C. reaction mixture. After 30 minutes, the reaction mixture was vacuum filtered, the filtrate collected and the solvent removed to reveal to yield the free carboxylate as a white solid residue. Purification was performed using a chromatron with ethyl acetate/methylene chloride (20/80) as the solvent system. The yield was 43%.

Example VII

Polymerization of Poly(1,8-bis(o-dicarboxyphenyl)octane)

To remove the benzyl protecting groups, the 1,8-bis[(benzylcarboxy)carboxyphenyl]octane dicarboxylic acid ester of Example VI (0.06000 g, 0.9620 mmole) was dissolved in methylene chloride in a reaction flask (60.00 mL). The catalyst Pd—C (10%, 1.200 g) was added to the reaction flask. After 30 minutes, the reaction was complete. The reaction mixture was filtered and the solvent removed to yield the free dicarboxylic acid as a white solid residue which was recrystallized using petroleum ether and methylene chloride. The yield was 45%.

The dicarboxylic acid was acetylated using the methods described in Example II and the acetylated dicarboxylic acid was then polymerized using the methods described in Example III. The resulting polymer had a $M_w$ of 3,000 daltons and a polydispersity of 1.40.

Subsequent polymerizations yielded polymers with $M_w$'s ranging from 2,000 to 5,000 daltons with corresponding polydispersities of approximately 1.40.

The poly(anhydride esters) of Example VII were compression molded into circular discs and placed in phosphate buffered saline solution under acidic, neutral and basic conditions. Over the course of a three-week degradation study, the polymers in the acidic and neutral solutions showed no observable changes, whereas the polymer in the basic media showed significant morphological changes over time.

Example VIII

Preparation of Poly[(1,8-bis(o-dicarboxyphenyl)octane)-(1,6-bis(p-carboxyphenoxy)hexane] copolymers The 1,8-bis(o-dicarboxyphenyl)octane of Example II was copolymerized with 1,6-bis(p-carboxyphenoxy)hexane using the methods described in Example III. In an in vivo mouse study, each mouse was implanted with 2 polymers, the copolymer of Example VIII and poly(1,6-bis(p-carboxyphenoxy)hexane). Each polymer was compression molded for 1 to 5 minutes at 1 to 20 K psi depending on the thickness of polymer needed. The polymer was placed under the palatal gingival mucosa adjacent to the first maxillary molars. The mice were sacrificed at 1, 4 and 10 day intervals and demonstrated the biocompatibility an biodegradability in vivo of the polymers of the present invention, with salicylic acid being released upon degradation, via hydrolysis of the polymer backbone.

STATEMENT OF INDUSTRIAL APPLICABLITY

The polymers of the present invention have a variety of pharmaceutical applications, particularly as anti-inflammatory compounds.

The foregoing examples and description of the preferred embodiment should be taken as illustrating, rather than as limiting, the present invention as defined by the claims. As would be readily appreciated, numerous variations and combinations of the features set forth above can be utilized without departing from the present invention as set forth in the claims. Such variations are not regarded as a departure from the spirit and the scope of the invention, and all such variations are intended to be included within the scope of the following claims.

What is claimed is:

1. An aromatic polyanhydride comprising a repeating unit having the structure:

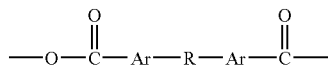

wherein Ar is an aromatic ring; R is $-Z_1-R_1-Z_1-$ substituted on each Ar ortho to the anhydride group; $R_1$ is a difunctional organic moiety; $Z_1$ is a difunctional moiety selected from the group consisting of ester, amides, urethanes, carbamates and carbonates; and Ar and R are selected so that when the aromatic polyanhydride hydrolyzes, a therapeutic salicylate, another non-steroidal anti-inflammatory, an antifibrotic aminobenzoate, or a vasoconstricting phenylethanolamine is formed.

2. The aromatic polyanhydride of claim 1, wherein Ar is a phenyl group.

3. The aromatic polyanhydride of claim 1, wherein $Z_1$ is an ester or amide group, and $R_1$ is selected from the group consisting of $(-CH_2-)_n$, $(-CH_2-CH_2-O-)_m$, $(-CH_2-CH_2-CH_2-O-)_m$, and $(-CH_2-CHCH_3-O-)_m$, wherein n is from 1 to 20, inclusive and m is selected so that $R_1$ has between 2 and 20 carbon atoms, inclusive.

4. The aromatic polyanhydride of claim 3, wherein n is 6.

5. The aromatic polyanhydride of claim 1, wherein $R_1$ is $-R_2-Z_2-R_3-$, wherein $R_2$ and $R_3$ are difunctional organic moieties and $Z_2$ is a difunctional moiety selected from the group consisting of esters, amides, urethanes, carbamates and carbonates.

6. The aromatic polyanhydride of claim 5, wherein $R_2$ and $R_3$ are independently selected from the group consisting of alkylene groups containing from 1 to 19 carbon atoms, $(-CH_2-CH_2-O-)_m$, $(-CH_2-CH_2-CH_2-O-)_m$, and $(-CH_2-CHCH_3-O-)_m$, wherein m is between 2 and 18, inclusive.

7. The aromatic polyanhydride of claim 1, wherein Ar and R are selected so that said aromatic polyanhydride hydrolyzes to form a therapeutic salicylate.

8. The aromatic polyanhydride of claim 7, wherein the salicylate is selected from the group consisting of thymotic acid, 4-sulfanilamidosalicylic acid, salicylsulfuric acid, salsalate, mesalamine, gentisic acid, enfenamic acid, salicylic acid, cresotic acid, aminosalicylic acid and aminophenylacetic acid.

9. An implantable medical device comprising the aromatic polyanhydride of claim 1.

10. The implantable medical device of claim 9, wherein said device is a scaffolding implant for tissue reconstruction.

11. The implantable medical device of claim 9 comprising a biologically or pharmaceutically active compound in combination with said aromatic polyanhydride, wherein said active compound is present in amounts sufficient for therapeutically effective site-specific or systemic drug delivery, wherein Ar and R are selected so that when the aromatic polyanhydride hydrolyzes, a therapeutic salicylate is formed.

12. A method for site-specific or systemic drug delivery comprising implanting in the body of a patient in need thereof an implantable drug delivery device comprising a therapeutically effective amount of a biologically or pharmaceutically active compound in combination with the aromatic polyanhydride of claim 1.

13. A drug delivery system comprising the aromatic polyanhydride of claim 1 physically admixed with a biologically or pharmaceutically active agent.

14. A drug delivery system comprising a biologically or pharmaceutically active agent physically embedded or dispersed into a polymeric matrix formed from the aromatic polyanhydride of claim 1.

15. A drug delivery system comprising a biologically or pharmaceutically active agent covalently bonded to the aromatic polyanhydride of claim 1.

16. An ortho-substituted bis-aromatic dicarboxylic acid anhydride having the structure:

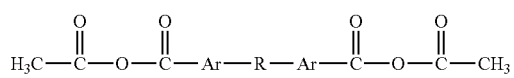

wherein Ar is an aromatic ring; R is $-Z_1-R_1-Z_1-$ substituted on each Ar ortho to the anhydride group; $R_1$ is a difunctional organic moiety; $Z_1$ is a difunctional moiety selected from the group consisting of ester, amides, urethanes, carbamates and carbonates; and Ar and R are selected so that when the ortho-substituted bis-aromatic dicarboxylic acid anhydride hydrolyzes, a therapeutic salicylate, another non-steroidal anti-inflammatory, an antifibrotic aminobenzoate, or a vasoconstricting phenylethanolamine is formed.

17. The acid anhydride of claim 16, wherein Ar is a phenyl group.

18. The acid anhydride of claim 17, wherein $Z_1$ is an ester or amide group, and $R_1$ is selected from the group consisting of $(-CH_2-)_n$, $(-CH_2-CH_2-O-)_m$, $(-CH_2-CH_2-CH_2-O-)_m$, and $(-CH_2-CHCH_3-O-)_m$, wherein n is from 1 to 20, inclusive, and m is selected so that $R_1$ has between 2 and 20 carbon atoms, inclusive.

19. The acid anhydride of claim 18, wherein n is 6.

20. An ortho-substituted bis-aromatic dicarboxylic acid having the structure HOOC—Ar—R—Ar—COOH, wherein Ar is an aromatic ring; R is $-Z_1-R_1-Z_1-$ substituted on each Ar ortho to the anhydride group; $R_1$ is a difunctional organic moiety; $Z_1$ is a difunctional moiety selected from the group consisting of ester, amides, urethanes, carbamates and carbonates; and Ar and R are selected so that when the ortho-substituted bis-aromatic dicarboxylic acid anhydride hydrolyzes, a therapeutic salicylate, another non-steroidal anti-inflammatory, an antifibrotic aminobenzoate, or a vasoconstricting phenylethanolamine is formed.

21. The dicarboxylic acid of claim 20, wherein Ar is a phenyl group.

22. The dicarboxylic acid of claim 21, wherein $Z_1$ is an ester or amide group, and $R_1$ is selected from the group consisting of $(-CH_2-)_n$, $(-CH_2-CH_2-O-)_m$, $(-CH_2-CH_2-CH_2-O-)_m$ and $(-CH_2-CHCH_3-O-)_m$, wherein n is from 1 to 20, inclusive, and m is selected to that $R_1$ has between 2 and 20 carbon atoms, inclusive.

23. The dicarboxylic acid of claim 22, wherein n is 6.

24. A method for treating inflammation comprising administering to a patient in need thereof a quantity of the aromatic polyanhydride of claim 1, wherein Ar and R are selected so that a therapeutic salicylate or phenyl or naphthyl propionic acid is formed at the site of said inflammation in an amount effective to relieve said inflammation when the aromatic polyanhydride hydrolyzes.

25. The method of claim 24, wherein Ar and R are selected so that said aromatic polyanhydride hydrolyzes to form a therapeutic salicylate selected from the group consisting of thymotic acid, 4-sulfanilamidosalicylic acid, salicylsulfuric acid, salsalate, mesalamine, gentisic acid, enfenamic acid, salicylic acid, cresotic acid, aminosalicylic acid and aminophenylacetic acid.

26. A therapeutic method comprising administering to a patient in need thereof an effective amount of an aromatic polyanhydride according to claim 1, wherein Ar and R are selected so that when said aromatic polyanhydride hydrolyzes, an antifibrotic aminobenzoate or a vasonconstricting phenylethanolamine is formed.

27. An anti-inflammatory dosage form comprising an effective amount of the aromatic polyanhydride of claim 7, and a pharmaceutically acceptable excipient.

28. The dosage form of claim 27, wherein said aromatic polyanhydride hydrolyzes to form a therapeutic salicylate selected from the group consisting of thymotic acid, 4-sulfanilamidosalicylic acid, salicylsulfuric acid, salicylic acid, salsalate, mesalamine, gentisic acid, enfenamic acid, cresotic acid, aminosalicylic acid and aminophenylacetic acid.

29. The dosage form of claim 27, further comprising a second therapeutic agent to be administered in combination with said polyanhydride.

30. A method for treating digestive inflammation comprising administering to a patient in need thereof a quantity of the aromatic polyanhydride of claim 7 in an amount effective to relieve said inflammation.

31. The method of claim 30, wherein said therapeutic salicylate is selected from the group consisting of thymotic acid, 4-sulfanilamidosalicylic acid, salicylsulfuric acid, salicylic acid, salsalate, mesalamine, gentisic acid, enfenamic acid, cresotic acid, aminosalicylic acid and aminophenylacetic acid.

32. A therapeutic treatment method comprising administering to a patient in need thereof an effective quantity of an aromatic polyanhydride according to claim 1, wherein Ar and R are selected so that said aromatic polyanhydride hydrolyzes to form an antifibrotic aminobenzoate or a vasoconstricting phenylethanolamine.

33. The aromatic polyanhydride of claim 3, wherein Ar and R are selected so that said aromatic polyanhydride hydrolyzes to form a therapeutic salicylate.

34. A film, coating, dish or sponge comprising the polymer of claim 1.

35. A film, coating, dish or sponge comprising the polymer of claim 33.

36. A film, coating, dish or sponge comprising the polymer of claim 8.

37. A medical implant having a coating that comprises a polymer of claim 1.

38. A medical implant having a coating that comprises a polymer of claim 33.

39. A medical implant having a coating that comprises a polymer of claim 8.

40. The medical implant of claim 35 that is selected from the group consisting of a vascular graph, a stent, a bone plate, a suture, an implantable sensor, an implantable drug delivery device or a stent for tissue regeneration.

41. The medical implant of claim 38 that is selected from the group consisting of a vascular graph, a stent, a bone plate, a suture, an implantable sensor, an implantable drug delivery device or a stent for tissue regeneration.

42. The polymer of claim 7 that is processed using solvent casting.

* * * * *